US008544132B2

(12) United States Patent
Gatzemeyer et al.

(10) Patent No.: US 8,544,132 B2
(45) Date of Patent: Oct. 1, 2013

(54) INTERACTIVE TOOTHBRUSH AND REMOVABLE AUDIO OUTPUT MODULE

(76) Inventors: John Gatzemeyer, Hillsborough, NJ (US); Eduardo Jimenez, Manalapan, NJ (US); Robert Moskovich, East Brunswick, NJ (US); Kenneth Waguespack, North Brunswick, NJ (US); James Kemp, Basking Ridge, NJ (US); Douglas Hohlbein, Hopewell, NJ (US); Mary Horchos, Metuchen, NJ (US); Thomas Mintel, Rahway, NJ (US)

( * ) Notice: Subject to any disclaimer, the term of this patent is extended or adjusted under 35 U.S.C. 154(b) by 209 days.

(21) Appl. No.: 12/991,624

(22) PCT Filed: May 7, 2008

(86) PCT No.: PCT/US2008/062864
§ 371 (c)(1),
(2), (4) Date: Jan. 28, 2011

(87) PCT Pub. No.: WO2009/136918
PCT Pub. Date: Nov. 12, 2009

(65) Prior Publication Data
US 2011/0146016 A1    Jun. 23, 2011

(51) Int. Cl.
*A46B 15/00*    (2006.01)
(52) U.S. Cl.
USPC .............................. 15/22.1; 15/105
(58) Field of Classification Search
USPC .................. 15/105, 167.1, 21.1–29
See application file for complete search history.

(56) References Cited

U.S. PATENT DOCUMENTS

| | | |
|---|---|---|
| 1,986,955 A | 1/1935 | Bedell |
| 2,877,477 A | 3/1959 | Levin |
| 2,947,013 A | 8/1960 | Silverman |
| 3,027,507 A | 3/1962 | Hubner |
| D210,349 S | 3/1968 | Boldt |
| 3,458,794 A | 7/1969 | Bohnstedt |
| 4,075,458 A | 2/1978 | Moyer |
| 4,341,230 A | 7/1982 | Siahou |
| 4,479,516 A | 10/1984 | Hunter |
| 4,603,448 A | 8/1986 | Middleton et al. |

(Continued)

FOREIGN PATENT DOCUMENTS

| | | |
|---|---|---|
| CA | 2267732 | 10/2000 |
| CA | 2409908 | 11/2002 |

(Continued)

OTHER PUBLICATIONS

International Search Report and Written Opinion in International Application No. PCT/US08/062864, mailed Oct. 5, 2009.

(Continued)

*Primary Examiner* — Shay Karls
(74) *Attorney, Agent, or Firm* — Ryan Flandro

(57) ABSTRACT

An oral care implement (100), comprising an oral care region (124,127) attached to a body (125), a portion (126) of the body being configured for gripping by a user; a memory configured to store a plurality of audio signals from an external signal source; at least one measurement component configured to measure a parameter of use of the oral care region (124,128); and a processor configured to change output of a first audio signal of the plurality of audio signals to a second audio signal of the plurality of audio signals based on the measured parameter from the at least one measurement component.

3 Claims, 7 Drawing Sheets

(56) References Cited

U.S. PATENT DOCUMENTS

| | | |
|---|---|---|
| 4,698,869 A | 10/1987 | Mierau et al. |
| 4,716,614 A | 1/1988 | Jones et al. |
| 4,744,124 A | 5/1988 | Wang |
| 4,764,961 A | 8/1988 | Hung |
| 4,766,630 A | 8/1988 | Hegemann |
| 4,788,734 A | 12/1988 | Bauer |
| 4,845,796 A | 7/1989 | Mosley |
| 4,866,807 A | 9/1989 | Kreit |
| D304,779 S | 11/1989 | Raphael et al. |
| D304,780 S | 11/1989 | Morris, Jr. |
| D304,781 S | 11/1989 | Hanson |
| 4,944,016 A | 7/1990 | Christian |
| 4,944,704 A | 7/1990 | Grace |
| 5,006,779 A | 4/1991 | Fenne |
| 5,044,037 A | 9/1991 | Brown |
| D321,986 S | 12/1991 | Snyder et al. |
| 5,115,533 A | 5/1992 | Hukuba |
| 5,133,102 A | 7/1992 | Sakuma |
| 5,165,131 A | 11/1992 | Staar |
| D340,455 S | 10/1993 | Christian |
| 5,259,086 A | 11/1993 | Fong |
| 5,314,336 A | 5/1994 | Diamond et al. |
| 5,335,798 A | 8/1994 | Bonwell |
| 5,337,435 A | 8/1994 | Krasner |
| 5,339,479 A | 8/1994 | Lyman |
| 5,341,534 A | 8/1994 | Serbinski et al. |
| D353,490 S | 12/1994 | Hartwein |
| D354,168 S | 1/1995 | Hartwein |
| 5,438,726 A | 8/1995 | Leite |
| D363,605 S | 10/1995 | Kou et al. |
| 5,493,747 A | 2/1996 | Inakagata et al. |
| 5,504,961 A | 4/1996 | Yang |
| D371,242 S | 7/1996 | Shimatsu et al. |
| D373,023 S | 8/1996 | Otero et al. |
| 5,544,382 A | 8/1996 | Giuliani |
| D375,841 S | 11/1996 | Serbinski et al. |
| 5,572,762 A | 11/1996 | Scheiner |
| 5,628,641 A | 5/1997 | Hahn |
| 5,673,451 A | 10/1997 | Moore et al. |
| 5,675,859 A | 10/1997 | Barre |
| 5,697,117 A | 12/1997 | Craft |
| D388,958 S | 1/1998 | Hartwein |
| 5,704,087 A | 1/1998 | Strub |
| 5,784,742 A | 7/1998 | Giuliani et al. |
| 5,786,749 A | 7/1998 | Johnson |
| D397,252 S | 8/1998 | Allende |
| 5,810,601 A | 9/1998 | Williams |
| D403,511 S | 1/1999 | Serbinski |
| 5,864,288 A | 1/1999 | Hogan |
| 5,894,453 A | 4/1999 | Pond |
| 5,901,397 A | 5/1999 | Hafele et al. |
| 5,924,159 A | 7/1999 | Haitin |
| 5,960,507 A | 10/1999 | Dutra |
| 5,974,616 A | 11/1999 | Dreyfus |
| 5,994,855 A | 11/1999 | Lundell et al. |
| 6,029,303 A | 2/2000 | Dewan |
| D426,708 S | 6/2000 | Francis |
| 6,081,957 A | 7/2000 | Webb |
| 6,115,477 A | 9/2000 | Filo |
| 6,154,912 A | 12/2000 | Li |
| D436,254 S | 1/2001 | Kiling et al. |
| 6,199,239 B1 | 3/2001 | Dickerson |
| 6,202,242 B1 | 3/2001 | Salmon et al. |
| 6,202,245 B1 | 3/2001 | Khodadadi |
| D440,766 S | 4/2001 | Hartwein et al. |
| 6,237,178 B1 | 5/2001 | Krammer et al. |
| 6,325,066 B1 | 12/2001 | Hughes |
| D453,996 S | 3/2002 | Kling et al. |
| D455,556 S | 4/2002 | Kling |
| 6,389,633 B1 | 5/2002 | Rosen |
| D458,028 S | 6/2002 | McCurrach |
| 6,397,424 B1 | 6/2002 | Leung |
| 6,421,866 B1 | 7/2002 | McDougall |
| D467,432 S | 12/2002 | Callendrille, Jr. |
| 6,536,068 B1 | 3/2003 | Yang |
| 6,554,619 B2 | 4/2003 | Williams |
| D474,895 S | 5/2003 | Breit |
| D475,529 S | 6/2003 | Wright et al. |
| 6,581,233 B1 | 6/2003 | Cheng |
| D476,485 S | 7/2003 | Mulder et al. |
| D478,423 S | 8/2003 | Mulder et al. |
| 6,606,755 B1 | 8/2003 | Robinson et al. |
| 6,611,780 B2 | 8/2003 | Lundell |
| 6,619,969 B2 | 9/2003 | Scheider |
| D480,563 S | 10/2003 | Hensel |
| 6,633,747 B2 | 10/2003 | Reiss |
| 6,648,641 B1 | 11/2003 | Viltro |
| D484,312 S | 12/2003 | Li |
| 6,658,687 B1 | 12/2003 | McDonald |
| D489,183 S | 5/2004 | Akahori et al. |
| D489,534 S | 5/2004 | Hensel |
| 6,731,213 B1 | 5/2004 | Smith |
| D492,118 S | 6/2004 | McCurrach et al. |
| D493,960 S | 8/2004 | Jimenez et al. |
| 6,779,216 B2 | 8/2004 | Davies et al. |
| D496,653 S | 9/2004 | Townsend et al. |
| 6,792,640 B2 | 9/2004 | Lev |
| 6,795,993 B2 | 9/2004 | Lin |
| 6,799,346 B2 | 10/2004 | Jeng et al. |
| 6,826,350 B1 | 11/2004 | Kashino et al. |
| D500,207 S | 12/2004 | Jimenez et al. |
| D500,208 S | 12/2004 | Vu |
| D500,209 S | 12/2004 | Kellogg |
| 6,836,918 B1 | 1/2005 | Wong |
| 6,845,537 B1 | 1/2005 | Wong |
| D502,601 S | 3/2005 | Lamason et al. |
| D503,537 S | 4/2005 | Lamason et al. |
| D503,852 S | 4/2005 | Hensel |
| 6,883,199 B1 | 4/2005 | Lundell et al. |
| 6,920,660 B2 | 7/2005 | Lam |
| 6,923,409 B2 | 8/2005 | Strunk |
| D510,930 S | 10/2005 | Deguchi |
| 6,952,855 B2 | 10/2005 | Lev et al. |
| 6,954,961 B2 | 10/2005 | Ferber et al. |
| D511,519 S | 11/2005 | Bone et al. |
| 6,960,170 B2 * | 11/2005 | Kuo ........................... 600/551 |
| D515,815 S | 2/2006 | Jimenez et al. |
| D515,816 S | 2/2006 | Jimenez et al. |
| 7,003,839 B2 | 2/2006 | Hafliger et al. |
| 7,013,522 B2 | 3/2006 | Kumagai |
| 7,049,790 B2 | 5/2006 | Pfenniger et al. |
| 7,055,531 B2 | 6/2006 | Rehkemper |
| 7,086,111 B2 | 8/2006 | Hilscher et al. |
| D529,044 S | 9/2006 | Andre et al. |
| D531,190 S | 10/2006 | Lee et al. |
| 7,120,960 B2 | 10/2006 | Hilscher et al. |
| D533,349 S | 12/2006 | Jimenez et al. |
| D533,720 S | 12/2006 | Vu |
| D534,726 S | 1/2007 | Vu |
| D534,728 S | 1/2007 | Vu |
| D534,921 S | 1/2007 | Andre et al. |
| D535,308 S | 1/2007 | Andre et al. |
| D538,267 S | 3/2007 | Christianson et al. |
| D538,297 S | 3/2007 | Ching |
| D539,813 S | 4/2007 | Chen |
| D539,817 S | 4/2007 | Reverberi |
| 7,418,757 B2 | 9/2008 | Gatzemeyer et al. |
| 2001/0004428 A1 | 6/2001 | Horng |
| 2002/0067084 A1 | 6/2002 | Jung |
| 2002/0092104 A1 | 7/2002 | Ferber et al. |
| 2002/0174498 A1 | 11/2002 | Li |
| 2003/0017874 A1 | 1/2003 | Jianfei |
| 2003/0221269 A1 | 12/2003 | Zhuan |
| 2003/0232303 A1 | 12/2003 | Black |
| 2004/0000017 A1 | 1/2004 | Kumagai |
| 2004/0074026 A1 | 4/2004 | Blaustein et al. |
| 2004/0123409 A1 | 7/2004 | Dickie |
| 2004/0134000 A1 | 7/2004 | Hilfinger et al. |
| 2004/0163191 A1 | 8/2004 | Cuffaro et al. |
| 2004/0255409 A1 | 12/2004 | Hilscher |
| 2005/0000537 A1 | 1/2005 | Junkins |
| 2005/0011022 A1 | 1/2005 | Kwong |
| 2005/0022322 A1 | 2/2005 | Jimenez et al. |
| 2005/0066461 A1 | 3/2005 | Chang |

| | | | | | | |
|---|---|---|---|---|---|---|
| 2005/0144744 A1 | 7/2005 | Thiess et al. | | EP | 0634151 | 1/1995 |
| 2005/0150067 A1 | 7/2005 | Cobabe et al. | | EP | 1609389 | 12/2005 |
| 2005/0152231 A1 | 7/2005 | Yeh | | EP | 1698252 A | 9/2006 |
| 2005/0172433 A1 | 8/2005 | Oliver | | JP | 1008914 | 1/1989 |
| 2005/0204490 A1 | 9/2005 | Kemp et al. | | JP | 11-352981 | 12/1999 |
| 2005/0278882 A1 | 12/2005 | Drzewiecki et al. | | JP | 2003180717 | 7/2003 |
| 2005/0283929 A1 | 12/2005 | Jimenez et al. | | JP | 2004065838 | 3/2004 |
| 2006/0037158 A1 | 2/2006 | Foley et al. | | JP | 2004105246 | 4/2004 |
| 2006/0048315 A1 | 3/2006 | Chan et al. | | JP | 2006-331554 | 12/2006 |
| 2006/0057513 A1 | 3/2006 | Ito et al. | | KR | 10-2007-0107197 A | 11/2007 |
| 2006/0104456 A1 | 5/2006 | Filo et al. | | RU | 2013968 | 6/1994 |
| 2006/0123570 A1 | 6/2006 | Pace et al. | | RU | 2216295 | 11/2003 |
| 2006/0130253 A1 | 6/2006 | Rycroft | | TW | 122656 | 11/1989 |
| 2006/0150350 A1 | 7/2006 | Pfenniger et al. | | TW | 373901 | 2/2010 |
| 2006/0179591 A1 | 8/2006 | Spooner | | WO | WO97/00650 | 1/1997 |
| 2007/0039109 A1 | 2/2007 | Nanda | | WO | WO98/55274 | 12/1998 |
| 2007/0074359 A1 | 4/2007 | O'Lynn | | WO | WO99/32011 | 7/1999 |
| 2007/0094822 A1* | 5/2007 | Gatzemeyer et al. ........... 15/105 | | WO | WO00/74591 | 12/2000 |
| 2007/0190509 A1* | 8/2007 | Kim ............................. 434/263 | | WO | WO 01/45573 | 6/2001 |
| 2007/0192976 A1 | 8/2007 | Gatzemeyer | | WO | WO03/085670 | 10/2003 |
| 2007/0261185 A1 | 11/2007 | Guney et al. | | WO | WO2004/026077 | 4/2004 |
| 2008/0028553 A1 | 2/2008 | Batthauer | | WO | WO2004/098445 | 11/2004 |
| 2009/0215015 A1* | 8/2009 | Chu ............................. 434/238 | | WO | WO 2005/000150 | 1/2005 |
| | | | | WO | WO2005/074745 | 8/2005 |
| FOREIGN PATENT DOCUMENTS | | | | WO | WO2006/002101 | 1/2006 |
| CA | ID98346 | 1/2004 | | WO | WO2006/057513 | 6/2006 |
| CA | ID102709 | 1/2004 | | WO | WO2006/065159 | 6/2006 |
| CA | 2499371 | 4/2004 | | WO | WO2006/119205 | 11/2006 |
| CA | 2530337 | 1/2005 | | WO | WO2006/137648 | 12/2006 |
| CA | 2545676 | 5/2005 | | WO | WO 2006137648 A1 * | 12/2006 |
| CA | 2553568 | 9/2005 | | WO | WO2007/032015 | 3/2007 |
| CA | 2508994 | 12/2005 | | WO | WO2007/068984 | 6/2007 |
| CA | 2559039 | 6/2006 | | WO | WO2007/089638 | 8/2007 |
| CA | 2589817 | 6/2006 | | WO | WO2007/097886 | 8/2007 |
| CA | 2591798 | 7/2006 | | WO | WO2007/106757 | 9/2007 |
| CA | 2606805 | 11/2006 | | | | |
| CN | 2461373 | 11/2001 | | | | |
| CN | 2537277 | 2/2003 | | | | |
| CN | ZL03257211.5 | 5/2003 | | | | |
| CN | 1470205 | 1/2004 | | | | |
| CN | 2614048 | 5/2004 | | | | |
| CN | 3367849 | 5/2004 | | | | |
| CN | ZL03364715.1 | 5/2004 | | | | |
| CN | 1556994 | 12/2004 | | | | |
| CN | ZL200620092422 | 7/2006 | | | | |
| CN | 3666650 | 7/2007 | | | | |
| CN | ZL200630116898.5 | 7/2007 | | | | |
| DE | 3149233 | 4/1983 | | | | |
| DE | 19811676 | 9/1999 | | | | |
| DE | 29915858 U1 | 1/2000 | | | | |
| DE | 10254613 | 6/2004 | | | | |
| EP | 0435329 | 7/1991 | | | | |

OTHER PUBLICATIONS

International Search Report and Written Opinion in International Application No. PCT/US08/068298, mailed Jun. 10, 2009.

International Search Report in International Application No. PCT/US08/053920, mailed Sep. 29, 2008.

Partial International Search Report in International Application No. PCT/US08/062864, mailed Mar. 3, 2009.

Partial International Search Report in International Application No. PCT/US08/068298, mailed Feb. 18, 2009.

"iBrush—the toothbrush that makes you never want to stop brushing your teeth." Http://www.cs.chalmers.se.idc/ituniv/student/2003/ubicomp/ibrush.htm. Published 2003. Retrieved May 19, 2006.

* cited by examiner

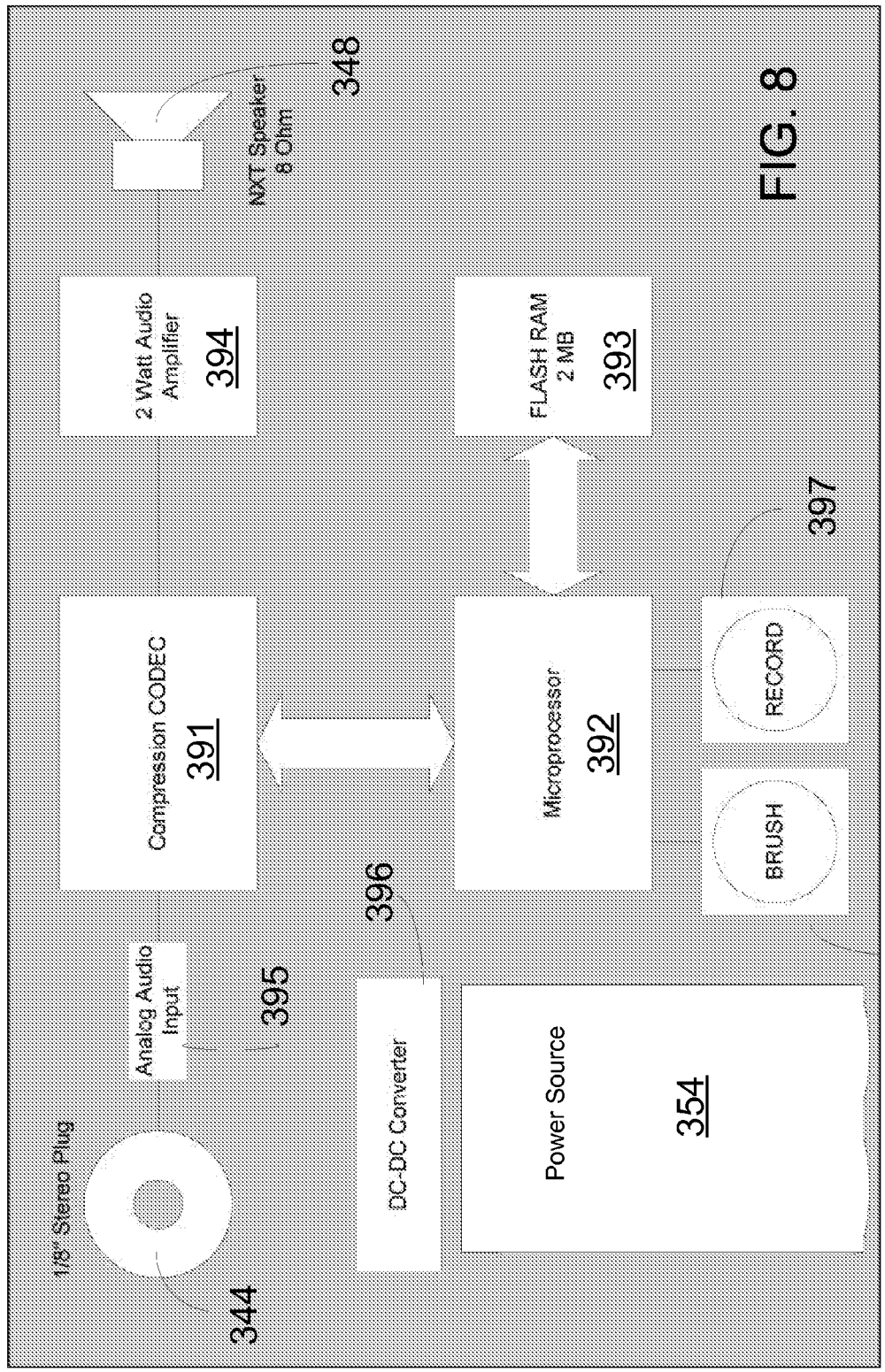

INTERACTIVE TOOTHBRUSH AND REMOVABLE AUDIO OUTPUT MODULE

CROSS-REFERENCE TO RELATED PATENT APPLICATIONS

The present application is a national stage entry under 35 U.S.C. 371 of International Patent Application No. PCT/US2008/062864, filed May 7, 2008, the entirety of which is hereby incorporated by reference.

BACKGROUND OF THE INVENTION

Aspects of the present disclosure relate to consumer products, including toothbrushes, and more particularly to a removable audio output module that can record and/or play music or other audio signals for use with various consumer products.

A small percentage of the population brushes their teeth for the dentist-recommended time of two minutes. This can be especially true of younger children and teenagers, who view tooth brushing as a mundane duty with few pleasurable aspects.

In addition, healthy cleaning habits should extend beyond teeth cleaning. Recursive tasks such as washing dishes, cleaning a house, shampooing, and shaving, may be rushed and/or even neglected since little to no pleasure is often associated with them.

BRIEF SUMMARY OF THE INVENTION

Aspects of the invention enable a person to know when he/she has brushed his/her teeth for a period of time while enjoying an audio interlude.

In one aspect, an apparatus includes a connection component configured to connect the apparatus to any one of a plurality of different apparatuses.

In another aspect, a toothbrush includes at least one measurement component configured to measure a parameter of use of an oral care region of the toothbrush, and a processor configured to change the output of a first audio signal of a plurality of audio signals to a second audio signal of the plurality of audio signals based on the measured parameter.

In another aspect, a toothbrush includes a processor configured to receive first data from an external source and to output second data corresponding to the received first data to at least one output device; the at least output device is configured to output the second data from the processor.

A variety of different audio output module and toothbrush configurations are discussed herein, each creating an enjoyable environment during tooth brushing. These configurations advantageously provide improved oral hygiene for children and teenagers.

BRIEF DESCRIPTION OF THE DRAWINGS

FIG. 8 is an example functional block diagram of components of an audio output module in accordance with at least one aspect of the present invention.

DETAILED DESCRIPTION OF THE INVENTION

Figures 1, 2:
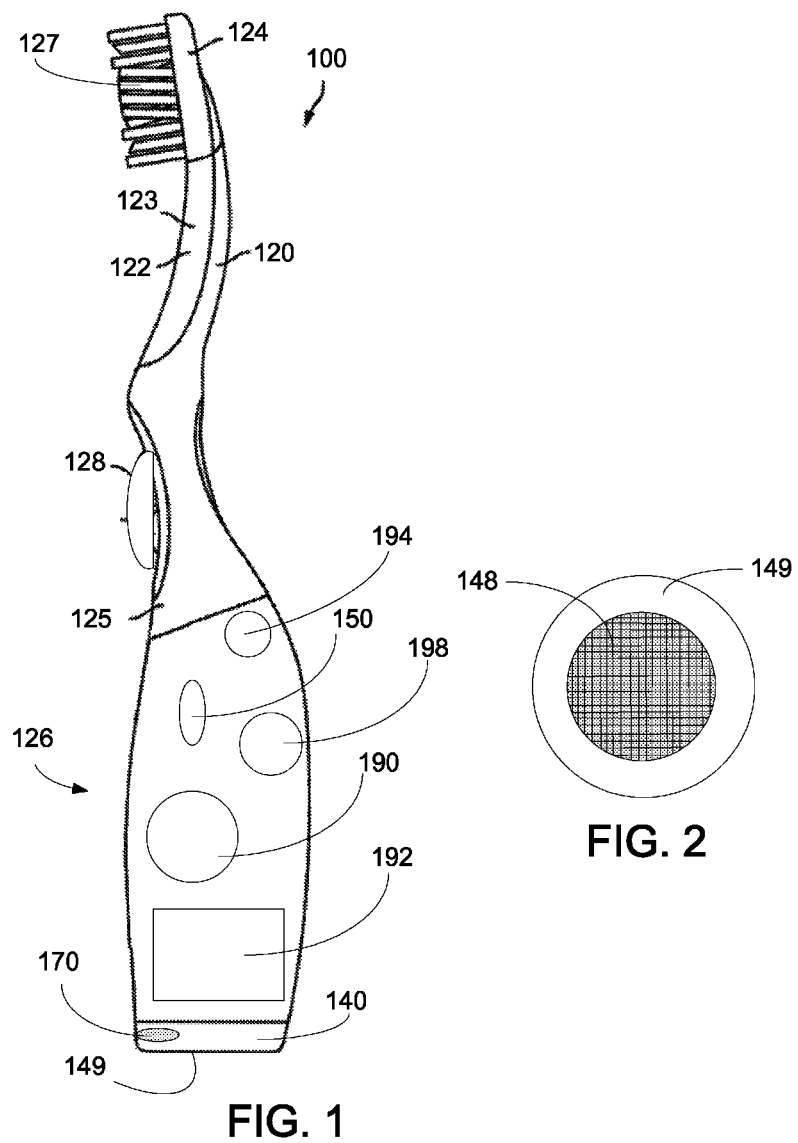
FIG. 1 is a side view of an example of a toothbrush assembly in accordance with at least one aspect of the invention.
FIG. 2 is a bottom view of the surface of the toothbrush of FIG. 1.

The following detailed description is not intended to be understood in a limiting sense, but to be examples of the disclosure presented solely for illustration thereof, and by reference to which in connection with the following description and the accompanying drawings one skilled in the art may be advised of the advantages and construction of the disclosure. In the various views of the drawings, like reference characters designate like or similar parts.

FIGS. 1-4 illustrate a toothbrush assembly 100 that may include a power toothbrush 120 having a body 125, a removable audio output module 140 that forms a portion of the handle 126, and an operation user interface, such as a button 128. The toothbrush 120 further includes a head 124 or oral care region having tooth cleaning elements 127. Head 124 may be replaceable, or it may be permanently attached to handle 126. As used herein, the term "tooth cleaning elements" or "cleaning elements" may include any type of structure that is commonly used or is suitable for use in providing oral health benefits (e.g., tooth cleaning, tooth polishing, tooth whitening, massaging, stimulating, etc.) by making contact with portions of the teeth and gums. Such tooth cleaning elements may include but are not limited to tufts of bristles that can be formed to have a number of different shapes and sizes and elastomeric cleaning members that can be formed to have a number of different shapes and sizes, or a combination of both tufts of bristles and elastomeric cleaning members.

The toothbrush 120 may be a powered toothbrush including a power source that drives a powered element, such as movable cleaning elements 127.

Figure 3:
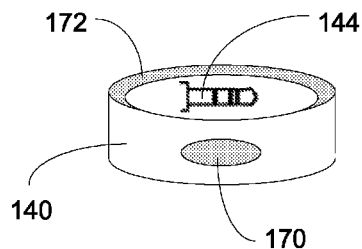
FIG. 3 is a side view of an example of an audio output module in accordance with at least one aspect of the invention.
Figure 4:
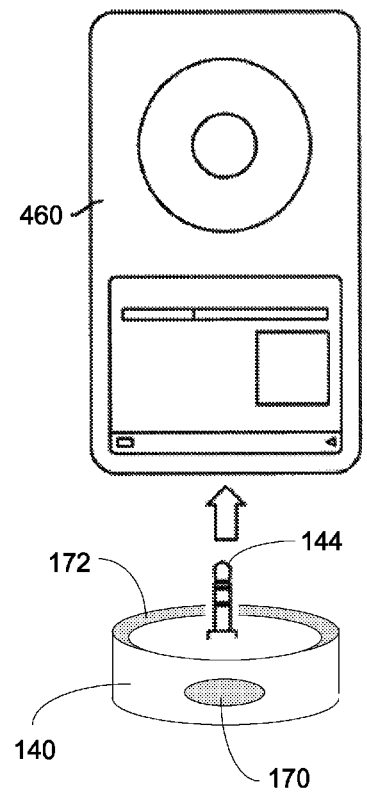
FIG. 4 is an exploded view of a connection arrangement of an audio output module of FIG. 3 and a signal source.

Referring to FIGS. 1-4, the removable audio output module 140 includes an input 144 for connecting to an audio device 460 and a digital memory device (not shown) for storing audio signals received via input 144 in digital form. Input 144 can take a variety of forms. For example, in one arrangement, input 144 may be a standard headphone jack (i.e., 2.5 mm). In another example, input 144 may comprise a USB connection. As shown in FIGS. 3-4, input 144 may be rotated or pivoted by a user into a vertical or receiving position, as shown in FIG. 4. In the vertical position, the input 144 may receive an audio signal provided from external audio device 460 so that audio signals are stored in memory in the audio output module 140.

Referring to FIG. 2, the removable audio output module 140 may include an output 148 in the form of a speaker positioned on the underside 149 of the module 140 for audibly transmitting the digitally stored audio signals to the user's ambient surroundings. In one example construction, the speaker may be of sealed construction for water resistance.

In one construction, the output 148 can be located at other parts of the audio output module 140. For example, speaker 148 may be configured on a sidewall of audio output module

140. In such a configuration, if the toothbrush 100 is upright so that underside 149 is against a base surface, such as a bathroom counter, music or other audio output still may be heard without a muffled sound as the audio signal hits the base surface. Still other constructions allow for multiple speakers 148 and/or a speaker system that may include components to output sound in multiple directions. In yet other constructions, toothbrush assembly 100 may include a speaker 190 within the handle 126. Speaker 190 may be configured to output audio signals stored within removable audio output module 140 when connected to internal components of toothbrush 120.

A microphone 194 may be included within the toothbrush assembly 100 and/or other components described herein, such as the removable audio output module 140. Microphone 194 may be configured to enable a user to input audio speech or sounds. In one example configuration using output module 140, microphone 194 may receive an audio signal of a user, such as a human voice and the received audio signal may be inputted into the removable audio output module 140. Input 144 of the removable audio output module 140 may be configured to connect to an internal contact within the handle 126 of toothbrush 100. When the microphone 194 receives an audio signal, the audio signal may be transferred through input 144 and stored within a digital memory of the removable audio output module 140.

In accordance with at least one aspect of the present disclosure, toothbrush assembly 100 may be configured to operate as an accessory to a mobile terminal, such as a cellular telephone and/or a personal digital assistant. Today, many individuals use wireless earpieces with their cellular telephones in order to talk and hear a conversation through their cellular telephone "hands-free." In addition, many individuals may work in an industry where business occurs while they sleep. Upon waking up and getting ready in the morning, an individual, in accordance with one or more aspects of the present disclosure, may utilize toothbrush 120 to make a telephone call, e.g., in order to retrieve voicemail messages.

Toothbrush 120 may include components to receive wireless communications from an external telephone, such as via BLUETOOTH® technology, and output audio through a speaker, such as side speaker 190 and receive audio from the user through a microphone, such as microphone 194. As such, a user can brush her teeth with toothbrush 100 while checking voicemail messages and/or interacting with another individual via an external cellular telephone. In yet another construction, toothbrush 120 may be a ZIGBEE complaint device. ZIGBEE pertains to an industry specification for a suite of communication protocols using small, low-power digital radio based on the IEEE 802.15.4 standard for wireless personal area networks, which is incorporated by reference herein. The radio-controlled configuration may include a transmitter and receiver operating at 2.4 GHz, but other frequencies may be implemented in different geographic regions. The data transfer rates can be 250 Kbs, but other data rates slightly lower or higher could be used. Various commercially available ZIGBEE complaint modules could be implemented. Other known wireless transmission protocols or wireless medium arrangements also can be employed. In another construction, toothbrush 120 may be configured to receive voice commands through microphone 194 to dial a specific number, such as a contact person or voicemail number, on an external cellular phone in communication with the toothbrush 120 via a wireless communication.

The audio output module 140 may further include a record button (not shown) for recording audio signals to a memory in the audio output module 140, and a play button 170 for playing the recorded audio signals. In at least one example configuration, the record functionality and the play functionality may be provided within a single button, such as button 170. In operation, the play feature may incorporate a timed playback aspect as described herein. An electrical power source, such as a battery or the like, may be provided in the audio output module 140 or toothbrush 120 for operation of the record and playback features as well as any powered element in the toothbrush 120. As an example of a powered element, a vibration generator 122 may be located in the neck 123 to generate vibrations in the head 124. The generator 122 can be powered by the power source.

Alternatively, the audio output module 140 and/or toothbrush 120 may mechanically connect into an outlet using a supplied cable connection (not shown). Other control configurations may be used. In accordance with at least one aspect of the present disclosure, the audio output module 140 of toothbrush 120 may be configured so that the functions associated with the record button and the play button 170 may be operational as a single button. In such a configuration, audio output module 140 may determine whether the input 144 is connected to a signal source 460, in order to receive audio signal(s) when the single button is activated, or whether the input 144 is connected to toothbrush 120 or connected to nothing at all, in order to play the audio signal(s) when the single button is activated. Although shown as a push button type input, button 128, the record button, and/or play button 170 may be any of a number of other types of input mechanisms or devices.

A user may connect toothbrush 120 to a signal source 460 (here shown as an digital media player for example in FIG. 4) and activate the signal transfer from the source 460 to a memory using a play button on the signal source (not shown) and a record button on the audio output module 140. The record button may be depressed or engaged once to record a certain period of music, such as three minutes for example, or it may be depressed or engaged for a period of time equal to the duration of music transferred.

The user then activates a timed playback of the stored music through the speaker 148 by pressing play button 170 to play music for, for example, two minutes upon pressing and holding button 170 for two seconds, or three minutes upon pressing and holding button 170 for three seconds. Other durations may be set, which can correlate with a time period other than two or three minutes, or it can designate a specific number of songs. Alternatively, toothbrush 120 may be configured so that a user may simply press the play button 170 if a timed playback is not desired. Nevertheless, while any type of musical or non-musical audio signals may be stored in the memory, the toothbrush 120 advantageously enables the user to play audio signals pleasurable to him or her. In this way, the user can have an enjoyable brushing experience and will likely brush his or her teeth for the entire playback duration.

Any audio content may be used. In various scenarios of use, for children and teens, the audio signals may comprise audio digital webcasts, musical segments from a radio, satellite audio device, computer network (e.g., Internet), or the user's audio collection and the like. In one scenario, for adults, the audio signals may comprise information-based news summaries or stock reports for example that are automatically downloaded from an on-line source such as a computer connected to the Internet or a local area network. The various functions of the toothbrush enhance the brushing experience and enable longer duration brushing for improved oral hygiene. An audio and/or video signal, can be stored in a digital memory of the toothbrush assembly 100, as long as the toothbrush assembly 100 includes an appropriate output to present the respective signal to a user. In one aspect, toothbrush assembly 100 also may include a display screen 192 to display video signals, e.g., music videos, stored in the audio output module 140.

Removable audio output module 140 and/or toothbrush 120 may include any of a number of different components to allow for various uses. For example, different removable audio output modules 140 may be utilized to allow for playing music or other audio from an AM or FM transmission. Components within toothbrush 120 may allow a user to tune to a specific frequency, such as an AM talk news radio station to listen while she brushes her teeth. Similarly, a removable audio output module may be configured to allow a user to output an FM country radio station to listen to music while she brushes her teeth. Different audio output modules 140 may be configured for different outputs.

Various types of operations may be utilized within the audio output module 140 alone, within the toothbrush 120 alone, or with a combination of the audio output module 140 and toothbrush 120 together. In other illustrative examples, toothbrush 120 and/or audio output module 140 may be configured to output Internet radio transmissions. A wireless connection to an external computer, and/or internal computer, connected to the Internet may allow for output of Internet radio through a speaker, such as speaker 148 of the audio output module and/or speaker 190 of the toothbrush 120. In still other illustrative examples, audio output module 140 and/or toothbrush 120 may be configured to output weather broadcasts. In such an example, audio output module 140 and/or toothbrush 120 may be configured to receive broadcasts of local, regional, or other weather reports and/or other weather related information. In addition, weather related video data also may be displayed to a user on display 192. Although not shown in the Figures, audio output module 140 may include a display for such a broadcast of video data as well. Still further, audio output module 140 and/or toothbrush 120 may be configured to download such weather broadcast data when not in use in order to conserve power and/or to have the data readily available for a user. For example, such data may be downloaded when the user may be asleep. Then, upon awaking and using the toothbrush, the weather broadcast data is readily available without the user having to wait for the data to be uploaded to the toothbrush and/or audio output module 140.

In another illustrative example, toothbrush 120 and/or audio output module 140 may be configured to include a digital camera. As shown in FIG. 1, toothbrush 120 may include a camera 198. a number of different camera technologies may be utilized. Although not shown, audio output module 140 also may include a camera. Such a camera may used to entertain a child when brushing his/her teeth to ensure that he/she brushes for the recommended two minutes. Pictures and/or video captured by the camera may be sent to a display, such as display 192, stored within a memory of the toothbrush 120 and/or audio output module 140, and/or may be transmitted wirelessly to an external storage device (not shown).

In yet another illustrative example, toothbrush 120 and/or audio output module 140 may be configured to include a thermometer. Although not shown in the Figures, a thermometer may be housed within the body of toothbrush 120 with a probe built within the head 124. As such, a parent and/or other individual may utilize the thermometer capability of toothbrush 120 and/or audio output module 140 to measure a temperature of a child or himself/herself. A temperature output may be given audibly through a speaker, such as speaker 148, and/or may be given visually through a display, such as display 192. The temperature data may be stored within toothbrush 120 and/or audio output module 140 and/or may be wirelessly transmitted to an external storage device (not shown). Such data may then be automatically sent to a doctor in case of emergency or other need. Any of a number of different thermometer types may be utilized within toothbrush 100 and/or audio output module 140.

In still another illustrative example, toothbrush 120 and/or audio output module 140 may be configured to include lights. Although not shown in the Figures, any of a variety of lights may be utilized, such as LEDs, within the body of and/or on the surface of toothbrush 120 and/or audio output module 140. Such lights may be used to entertain a child to ensure that he brushes his teeth the recommended two minutes per brushing session. The lights may be configured to change in response to music, to brushing a different section of the user's mouth, to a telephone call being received, to a new email message being received, and/or to any of a number of other uses.

In another illustrative example, toothbrush 120 and/or audio output module 140 may be configured to include one or more play lists of groups of audio signals to output in a specific order. Such play lists may be generated within an external audio device, such as device 460, and then transmitted to and stored within toothbrush 100 and/or audio output module 140. A user can choose a particular play list by an input button on the toothbrush, such as button 128 or 150, and/or on the audio output module, such as button 170. In at least one example, display 192 may be utilized to choose from a variety of different play lists. Similarly, display 192 may be utilized to choose from a variety of different audio signals, such a song, to output through a speaker, such as speaker 148 and/or 190.

In yet another illustrative example, toothbrush 120 and/or audio output module 140 may be configured to receive, display, and/or provide access to email for the user. Email messages may be outputted audibly through a speaker, such as speaker 148 and/or visually through a display, such as display 192. A user can choose a different message via an input button, such as button 128 and/or 150. Email messages may be wirelessly received from an external source, such as a computer of the user wirelessly communicating with the toothbrush 120 and/or audio output module 140. In still other examples, a user may receive reminders, whether through an email service or separately. Such reminders may be set by the user and/or another individual. For example, the user's spouse may leave a message to remind the user to take out the trash before leaving or to pick up the kids after school. In other examples, reminders may be received through an email service, e.g., to remind the user of an upcoming meeting or appointment.

Any number of types of external audio and/or video sources may be utilized including an MP3 player, a CD player, a cassette player, a computer, a satellite audio/video receiver, or handheld digital satellite audio device and/or other signal sources.

In the aspects of the oral device described below, the recording and/or storing audio signals, such as music, in a storage unit, for future playback is in accordance with the embodiments of FIGS. 1-4. Furthermore, the described signal source may be any external source as long as the signals are capable of being communicated and transferred from the source to the toothbrush assembly. Thus, the connection between the storage unit and the signal source does not have to be a direct physical connection, but could be a wireless connection that utilizes, for example, Bluetooth® technology or the like. The various illustrative arrangements of toothbrushes described herein each creates an environment that makes tooth brushing enjoyable and more likely to be maintained for at least the dentist-recommended period of time.

In one operation, the audio output module 140 may be removed from the body 125 (FIG. 2) and connected to a signal source 460 by a direct connection with the input 144. In accordance with at least one example, removable audio output module 140 may include a threaded connection area 172. In such an example, a user can rotate the bottom of the handle 126 of the toothbrush 100 around the threaded connection area 172. A connection (not shown) may be located within the interior of the handle 126 for connecting the input 144 of the removable audio output module 140 to other internal components of the toothbrush 120.

In the embodiments of FIGS. 1-4 the input 144 generally comprises a headphone jack that extends outwardly from the audio output module 140 when in use, as shown in FIG. 4. The input 144 may be concealed within the body of the audio output module 140 when the audio output module 140 is connected to toothbrush handle 126. Nevertheless, other input connections are contemplated, such as a Universal Serial Bus (USB) connector/adapter, which may be covered during use of the toothbrush 120 by a protecting cap (not shown), and which may function to both communicate with a signal source 460 and a power source such as a recharging base (not shown). In this regard, the physical attachment of the input 144 to the body 125 need not result in signals being transferred from the audio output module 140 to the body 125. The outward extension of the input 144 allows the audio output module 140 to be directly connected or attached to the source 460 at a convenient location. The record button and play button 170 function in a similar manner as described above, and a timed playback feature could be incorporated as also described above.

Button 128 may be configured to operate as a single input button for multiple modes of operation of the toothbrush 120. Button 128 may be configured to operate in a number of different manners depending on the length of time the button 128 is depressed, how many times the button 128 is depressed, and/or the area of button 128 that is depressed. Button 128 may be configured to operate motorized elements of toothbrush 120 and output music and/or other audio in accordance with one or more modes of operation.

In accordance with one mode, the toothbrush 120 may be motorized for movement of one or more cleaning elements and music and/or other audio may be outputted from a speaker at a high volume. In accordance with another mode, the toothbrush 120 may be motorized for movement of one or more cleaning elements and music and/or other audio may be outputted from a speaker at a low volume. In accordance with still another mode, the toothbrush 120 may be motorized for movement of one or more cleaning elements and no music and/or other audio may be outputted from a speaker. In accordance with yet another mode, the toothbrush 120 may not be motorized for movement of one or more cleaning elements and music and/or other audio may be outputted from a speaker.

Any of a number of different operations of the motorized cleaning elements of the toothbrush 120 and/or the music or other audio output may be configured for a mode of operation in accordance with one or more aspects of the present disclosure described herein. For example, one mode of operation may be to output music or other audio from a particular file, such as a particular play list of the user that is stored in the toothbrush 120. In another mode of operation, the speed of the motorized cleaning elements of the toothbrush 120 may change in accordance with music tempo, volume, or other features. Any of a number of different modes of operation of the moving elements of toothbrush 120 and/or the music or other audio output from toothbrush 120 may be utilized in accordance with one or more aspects of the present disclosure.

Any of a number of different modes of operation of the toothbrush 120 at certain speeds and/or music or other audio output at certain volumes may be utilized in accordance with one or more aspects of the present disclosure described herein and the present disclosure is not limited to the illustrative examples provided.

Figure 5:
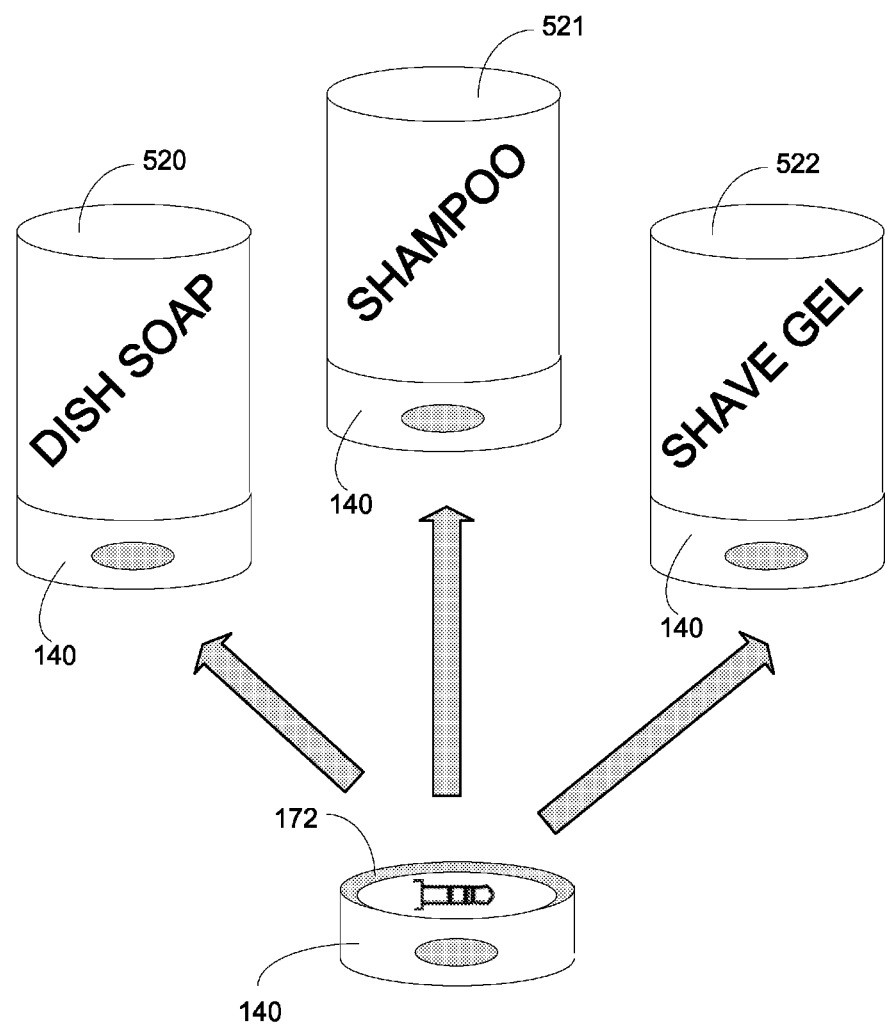
FIG. 5 is an exploded view of an example of attachments for the audio output module of FIG. 3.

FIG. 5 is an exploded view of an example of attachments for a removable audio output module 140 described herein. As shown, removable audio output module 140 may be configured to be physically attached to and be removed from one or more consumer products. Any of a number of different products may be included and those shown in FIG. 5 are but a few examples. Removable audio output module 140 may be connected to dish soap product 520 by screwing the bottom of the product 520 around the threaded connection area 172 of the removable audio output module 140. As shown, removable audio output module 140 may be connected to a number of different consumer products including a shampoo container product 521 and a shave gel container product 522. Additional container products may be connected as well including, but not limited to, hand soap containers, deodorant containers, conditioner containers, hair gel containers, and toothpaste containers. As such a user can interchange use of the removable audio output module with various tasks related to personal grooming and/or household cleaning.

Figure 6:
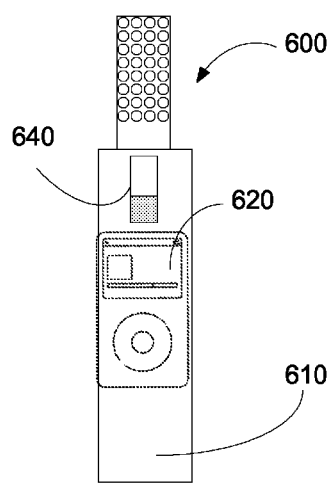
FIG. 6 is a front view of an example of a toothbrush in accordance with at least one aspect of the invention.
Figure 7A:
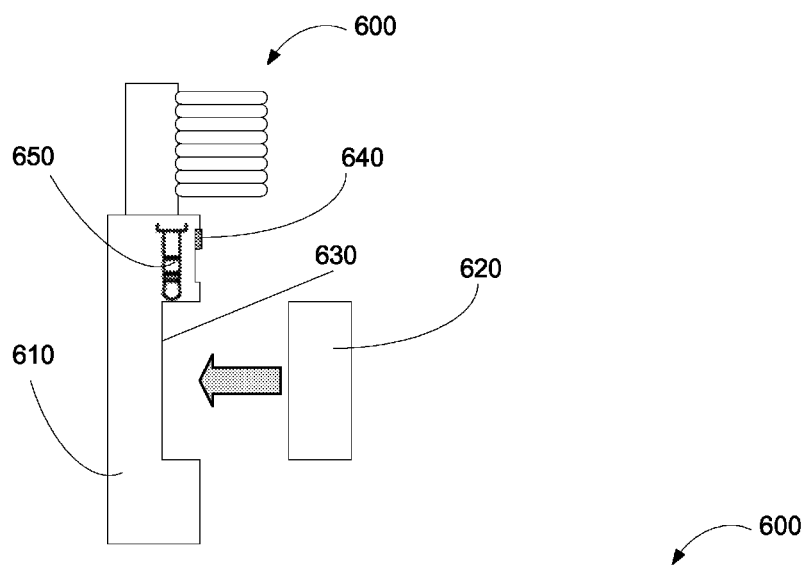
FIGS. 7A-7B are side views of a connection arrangement of a toothbrush and a signal source.
Figure 7B:
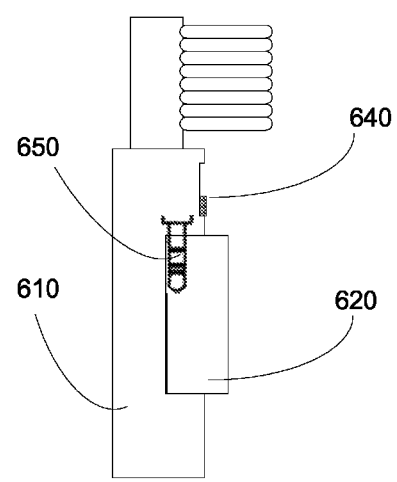

FIGS. 6-7B illustrate another toothbrush assembly in accordance with at least one aspect of the present disclosure. The toothbrush assembly may include a power toothbrush 600 having a body 610, a removable audio output unit 620 that may be inserted into an opening or cavity 630 of body 610, and a switch 640. The toothbrush 600 further may include a head having cleaning elements. The cleaning elements may comprise any known cleaning elements used in toothbrushes or other oral care implements, such as, but not limited to nylon bristles, tufts of bristles, bristle walls, elastomeric elements, and the like. The toothbrush 600 may be a power toothbrush including a motor/power source (e.g., motor and battery combination, for example) that drives a shaft or rotor for a powered element, such as movable cleaning elements.

The removable audio output unit 620 may be any of a number of different audio output devices, such as an MP3 player. Removable audio output unit 620 is configured to be a portion of the outside surface of the body 610 or a portion of body 610.

Toothbrush 600 may further include an input 650 for connecting the toothbrush 600 to the removable audio output unit 620. Input 650 may be a standard headphone jack. Toothbrush 600 may include a slideswitch 640 to allow the user to lower the input 650 into a headphone port on the removable audio unit 620 when the removable audio unit 620 is included within the opening 630 of the toothbrush. In this example, when slideswitch 640 is in an upward position, as shown in FIG. 7A, the input 650 remains within the body 610 of toothbrush 600. As such, the input 650 is less likely to be inadvertently broken off or damaged. When slideswitch 640 is in a downward position, as shown in FIG. 7B, the input 650 slides down for connection to the headphone port of the audio unit 620 when the audio unit 620 is within the opening 630 of the toothbrush 600. In such a configuration, a speaker (not shown) on the toothbrush 600 may act as headphones to the audio unit 620 and output audio signals while the user is brushing her teeth. Such a toothbrush 600 may be configured to operate with a plurality of audio units 620 manufactured and/or sold by other companies. For example, an APPLE® Shuffle® unit may be the audio unit 620.

FIG. 8 illustrates an exemplary block diagram of components of an audio output module in accordance with at least one aspect of the present disclosure. One or more of the components of FIG. 8 may be included within one or more printed circuit boards. An illustrative printed circuit board may be 18 mm×50 mm with a 16 kHz sample rate. Nevertheless, other sizes may be used. As shown, the components of a storage unit may include an input plug 344 in the form of a ⅛ inch stereo plug coupled to an analog audio input component 395. An integrated speaker 348, such as an 8 Ohm NXT speaker, may be coupled to an amplifier 394, such as a 2 Watt audio amplifier. Input received from the input plug 344 through the analog audio input component 395 is sent to a compression CODEC 391. Signal(s) for output are sent to the speaker 348 though the amplifier 394 from the compression CODEC 391. Compression CODEC 391 is shown in communication with a microprocessor 392.

Microprocessor 392 is configured to perform all of the functions for processing signal(s), performing computer-readable instructions, and reading from and writing to a memory 393. As shown, microprocessor 392 communicates with a memory 393, such as a 2 MB flash RAM. Audio signals received via input plug 344 are stored in memory 393 and may be outputted to speaker 348. Power is provided by one or more batteries 354 to supply electrical power through a DC to DC converter 396 to one or more components of the audio output module.

Recordation component 397 is shown coupled to microprocessor 392. Recordation component 397 may include instructions for the microprocessor 392 to record the audio signal(s) to memory 393 through input plug 344. Brush component 398 is shown coupled to microprocessor 392. Brush component 398 may include instructions for the microprocessor 392 to operate a motor (not shown) for a powered element (not shown) such as movable cleaning elements. Instructions with respect to recordation component 397 and/or brush component 398 may be included within memory 393 and/or some other memory, such as a ROM memory.

In one aspect, an oral care device, such as a toothbrush, a tongue cleaner, and/or a flossing device, may be configured to automatically record sound when the sound from a source device is detected. The sound from a source device triggers the oral care device to record the audio signal, i.e., the sound.

In one aspect, an oral care device may include an oral care region attached to a body with a portion of the body being configured for gripping by a user as described herein. This oral care device further may include a memory within the body of the device. The memory may be configured to store one or more audio signals.

A processor, which may be located within the body of the oral care device, may be configured to automatically record to the memory an audio signal from an external audio source, such as an MP3 player, a CD player, a radio, a television, and a person's voice. The processor may be configured to automatically record when the audio signal is detected. As such, the detection of the audio signal triggers the recording of the signal without any user selection to actually record the audio signal. Finally, a speaker may be included in the oral care device to output the stored audio signal. Any of a number of components described herein may be included in such an oral care device as well. Such components may include, but are not limited to a play button on the body configured to activate the processor to send the stored audio signal to the speaker, the oral care region including tooth cleaning elements, a power source within the body, the oral care region including at least one powered element, and various operational buttons to activate/deactivate powered elements and/or the output of stored audio signals.

Figure 9:
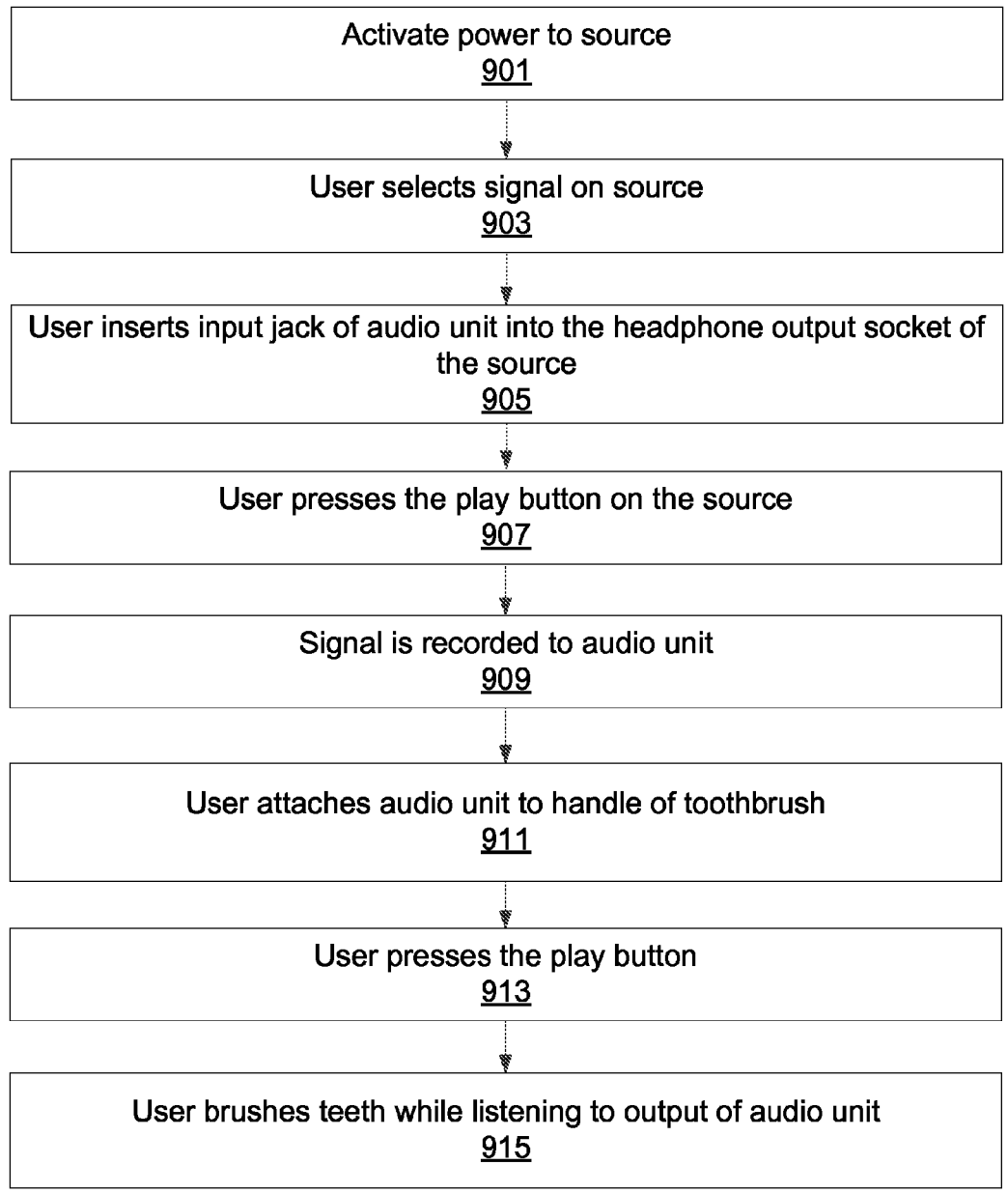
FIG. 9 is a flow chart of an illustrative method for transferring music or audio from a signal source to an audio output module.

FIG. 9 is a flow chart of an illustrative method for transferring music from a signal source to an audio output module in accordance with at least one aspect of the present disclosure. The process starts at step 901 where power to an external source, such as a music player, is activated by a user. Such may be the case when a user turns on the music player. At step 903, the user selects a particular signal on the source of interest. In one example, the user selects a particular 2-4 minutes song to be recorded. Proceeding to step 905, the user inserts the input headphone jack of a removable audio output module, such as input 144 of removable audio output module 140, into the headphone output socket of the source device, such as source device 460. At this point, although not shown, the user may set the output level of the source device to medium or low.

At step 907, the user presses the play button on the source device to play the selected song of interest. The storage unit may be configured to trigger recordation of the song when sound is detected. Alternatively, a record button, such as record button 150, associated with the toothbrush 120 may be depressed by the user to start the recordation process or a record button on the removable audio output module 140 may be depressed. In any configuration, at step 909, the selected signal of interest is recorded in the memory of the storage unit, such as memory 393. While the storage unit is recording, a previous file or song can be automatically overwritten. Upon completion of the recordation of the song and proceeding to step 911, the user attaches the removable audio output module to a toothbrush where the input jack of the audio output module may interface with a socket in the toothbrush. Alternatively, the audio output module may be physically screwed onto the toothbrush. Such an illustrative configuration is shown in FIG. 1.

At step 913, the user presses the play button on the removable audio output module. In one such example shown in FIG. 1, the user may depress button 170 to activate the output of music. Finally, at step 915, the user brushes her teeth with the toothbrush while watching and/or listening to output from the removable audio output module. For example, if a song of interest has been recorded, the song is outputted through a speaker, such as speaker 148. In one configuration, the time for the song may correlate to the desired amount of time for the user to brush her teeth, such as two minutes.

Aspects of the present disclosure provide for different audio signals to be outputted from a toothbrush, such as toothbrush 120, and/or an audio output module, such as audio output module 140, based upon operation of the toothbrush by a user. A default audio signal may be associated with a toothbrush for output. For example, when powered, a toothbrush may output a hum noise, as if to mimic the sound produced by an electric powered toothbrush. Then, the toothbrush may measure a load being applied to the head of the toothbrush, such as when the user is brushing her teeth. Upon measuring the load applied, the toothbrush may be configured to change an output signal in response. As such, the toothbrush now may output the sound of a drill since the user is brushing his/her teeth. Alternatively, the toothbrush may output the sound of cheers to congratulate the user on brushing her teeth.

Any of a number of different audio outputs may be assigned for any of a number of different measurements made by the toothbrush and/or audio output module. In one illustrative embodiment, a toothbrush or audio output module may be configured to measure the orientation of the toothbrush. For example, when the toothbrush is oriented in a manner to brush the top teeth, a first audio signal may be outputted. Then, when the toothbrush is flipped down to brush the user's bottom teeth, a second audio signal may be outputted. Still other configurations allow for measurement of the toothbrush cleaning the right side of the user's mouth or the left side of the user's mouth. As such, different audio outputs may be implemented for each measurement of an area. Therefore, the toothbrush in such a case is measuring the orientation of the toothbrush as a measured parameter of use.

In another illustrative embodiment, a toothbrush may include a tongue cleaner on the side of the toothbrush head opposite the cleaning bristles. In such an embodiment, a toothbrush or audio output module may be configured to measure the use of the tongue cleaner. When a user uses the tongue cleaner, another audio signal may be associated with the use. As such, when the user transitions from brushing her teeth to cleaning her tongue, the audio signal outputted from the toothbrush and/or audio output module may change in response. Signal outputs may be assigned to different measured values. As such, the same audio signal may be outputted in response to measuring use of the tongue cleaner portion and when the user is cleaning his/her top teeth, but a different audio signal may outputted when the user is brushing her bottom teeth.

In yet another illustrative example, a toothbrush or audio output module may be configured to measure a load applied to the bristles of the toothbrush. The audio signal may change between a first audio signal that may be a default signal, when no load is being applied, e.g., the user is not brushing her teeth, and a second audio signal when a load is being applied, e.g., the user is brushing her teeth. Still further, the audio signal may change based on the amount of load that is being applied. As such, a different audio signal, such as a warning alarm type of audio sound, may be outputted if the load being applied is considered to be too large, e.g., the user is applying too much pressure/force on his/her teeth with the toothbrush bristles. A sound may be configured to output an audio message to inform the user to apply more load or less load as needed.

Figure 10:
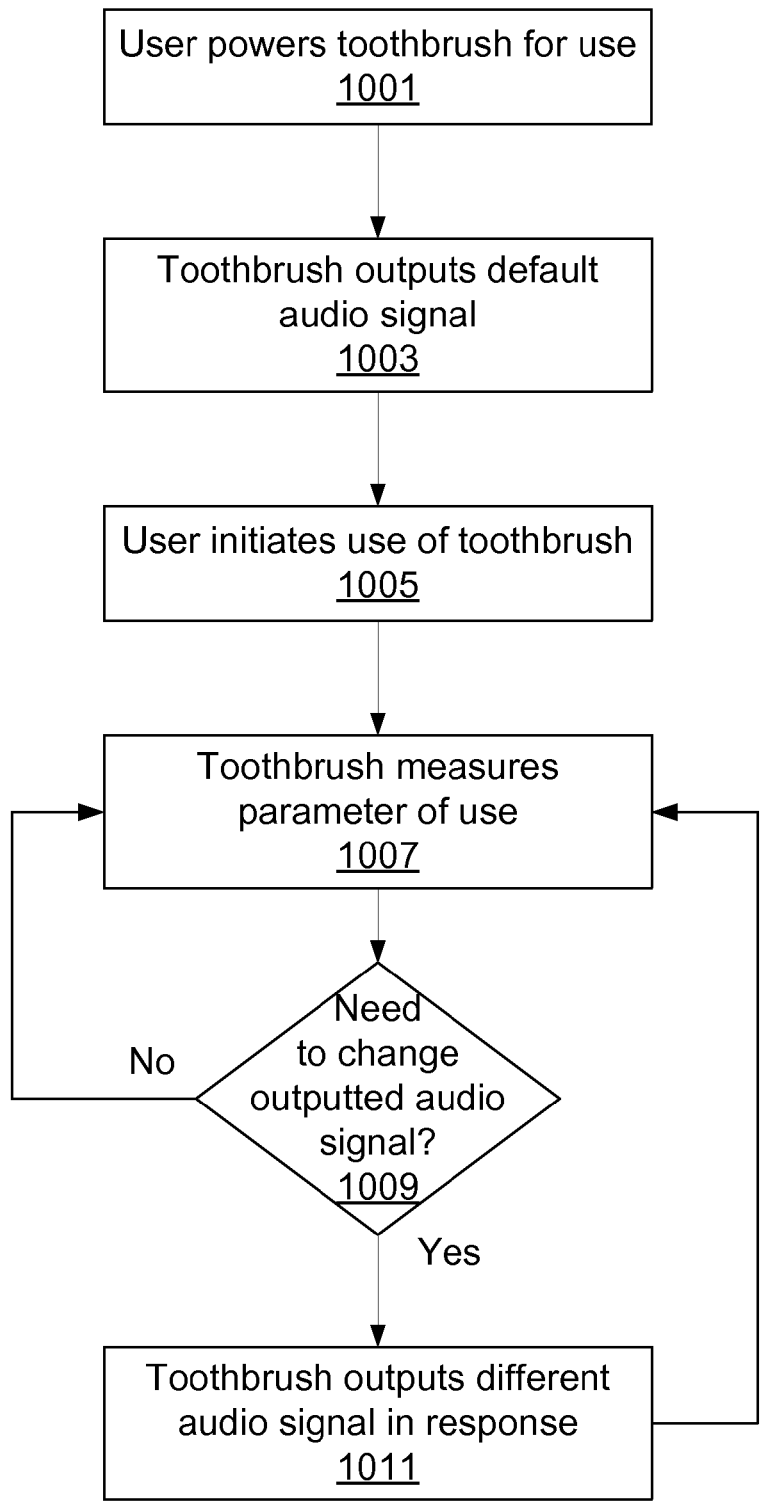
FIG. 10 is a flow chart of an illustrative method for changing a mode of operation of a toothbrush in accordance with at least one aspect of the invention.

FIG. 10 is a flow chart of an illustrative method for changing a mode of operation of a toothbrush described herein. The process starts and at step 1001, the user powers her toothbrush on for use. Proceeding to step 1003, the toothbrush may be configured to output a default audio signal. For example, after being powered on, with no load applied, the toothbrush may output a hum sound to mimic the sound of a traditional electric powered toothbrush or may output an audio message such as, "Hey! Let's get brushing!" In step 1005, the user initiates use of the toothbrush in some manner. For example, the user decides to start brushing her top teeth first. The process then moves to step 1007.

In step 1007, the toothbrush measures a parameter of use of the toothbrush. As described above, for example, the toothbrush may measure use of the tongue cleaner. In the example of FIG. 10, at step 1005, the user initiates use of the toothbrush, e.g., to start cleaning her top teeth. As such, in this example, at step 1007, the toothbrush measures the orientation of the toothbrush or other parameter, such as load being applied. From step 1007, the process moves to step 1009 where a determination is made as to whether a need exists to change the outputted audio signal in response to the measured parameter. For example, the toothbrush may be configured to output a different signal between no load applied and a load being applied, or between no load applied and orientation of the toothbrush to clean a user's top teeth. If no need to change the output signal is determined in step 1009, the process returns to step 1007. If a need to change in step 1009 does exist, the process moves to step 1011.

In step 1009, any of a number of different methods may be implemented to make such a determination. For example, software and/or firmware components associated with the toothbrush may match the measured parameter against a table of output signals based on one or more measured parameters. In response, instructions may be sent to a processor to change the audio signal output in response to the change in measured parameter.

Returning to step 1011, the toothbrush changes the outputted audio signal to a different audio signal. Then, the process returns to step 1007. Thereafter, if a user changes to a different use, such as brushing her bottom teeth, the toothbrush may measure the different use as a parameter in step 1007, may determine that a need exists to change the audio signal in step 1009, and may change the audio signal to a different audio signal in response in step 1011.

In another aspect, a vibratory device 122 can be provided to vibrate the toothbrush 120 or a portion thereof, such as the head 124 or a portion thereof. The vibration-producing device can be used to vibrate tooth cleaning elements 127 and/or soft tissue cleaning elements.

A wide variety of vibratory devices can be used to produce vibrations over a wide range of frequencies to meet the needs of a particular application. Various types of vibratory devices are commercially available, such as transducers. One example of a vibratory device provides frequencies in the range of about 100 to 350 kHz. The vibration frequencies may be of different waveforms, including sinusoid, square, sawtooth and the like. Nevertheless, other values and waveforms are possible. A vibratory device may be located in the head of the toothbrush or in the toothbrush neck. The vibratory device is powered by battery (and controlled by electronics on the circuit board or switching system) and is activated so as to induce vibrations in the head of the toothbrush and thereby enhance teeth-cleaning action imparted by the tooth cleaning elements. In alternate embodiments, a vibratory device may include a micro motor attached to a shaft, with the shaft coupled to an eccentric rotating about an axis parallel to the longitudinal axis of the toothbrush. In still other embodiments, a vibratory-producing device may include an eccentric that is driven by a micro motor in a translatory manner.

A switch, such as a button 128, toggle switch, rotating dial, or the like, can be provided for activating the vibratory device. A vibratory device often has a power source, such as a battery. Activating the switch can cause the vibration-producing device to operate for a user-defined interval (e.g., during the time that a button is depressed or a switch is in an engaged position), or alternatively can activate a timing circuit that causes the vibratory device to operate for a predetermined interval. If a timing circuit is used, the associated interval either may be preset or may be adjustable, e.g., by a user-activated rotating dial.

Designations such as "first" and "second" are for illustrative purposes and can be interchanged. While the disclosure has been described with respect to specific examples including presently preferred modes of carrying out the disclosure, those skilled in the art will appreciate that there are numerous variations and permutations of the above described systems and techniques. Thus, the spirit and scope of the disclosure should be construed broadly as set forth in the appended claims.

The invention claimed is:

1. An oral care implement, comprising:
an oral care region attached to a body, a portion of the body being configured for gripping by a user;
a memory configured to store a plurality of audio signals from an external signal source;
a module that is removable from the body, the module comprising the memory and a speaker;
an input that is connected to a slideswitch, the slideswitch moveable between: (1) a first position in which the input is entirely contained within the body; and (2) a second position in which the input extends front the body for connection to the module when the module is attached to the body;
at least one measurement component configured to measure a parameter of use of the oral care region; and
a processor configured to change output of a first audio signal of the plurality of audio signals to a second audio signal of the plurality of audio signals based on the measured parameter from the at least one measurement component.

2. The oral care implement of claim 1 wherein the body further comprises an opening within which the module is located when the module is attached to the body, and wherein the input extends into the opening when the slideswitch is in the second position.

3. The oral care implement of claim 1 wherein when the module is attached to the body and the slideswitch is in the second position, the audio signals stored within the memory of the module are output through a speaker on the oral care implement.

* * * * *